United States Patent
Onoda et al.

(10) Patent No.: US 12,319,571 B2
(45) Date of Patent: Jun. 3, 2025

(54) BIS(FLUOROSULFONYL)IMIDE COMPOUND AND METHOD FOR PRODUCING SAME

(71) Applicant: NIPPON SHOKUBAI CO., LTD., Osaka (JP)

(72) Inventors: Chie Onoda, Suita (JP); Takayuki Kobatake, Suita (JP); Hiromoto Katsuyama, Suita (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 706 days.

(21) Appl. No.: 17/613,460

(22) PCT Filed: May 1, 2020

(86) PCT No.: PCT/JP2020/018424
§ 371 (c)(1),
(2) Date: Nov. 22, 2021

(87) PCT Pub. No.: WO2020/235336
PCT Pub. Date: Nov. 26, 2020

(65) Prior Publication Data
US 2022/0212931 A1 Jul. 7, 2022

(30) Foreign Application Priority Data
May 23, 2019 (JP) ................. 2019-097130

(51) Int. Cl.
*C01B 21/086* (2006.01)
*C07C 255/03* (2006.01)
*C07F 3/02* (2006.01)

(52) U.S. Cl.
CPC .......... *C01B 21/086* (2013.01); *C07C 255/03* (2013.01); *C07F 3/02* (2013.01)

(58) Field of Classification Search
CPC ....... C01B 21/086; C07C 255/03; C07F 3/02; H01M 10/0525; H01M 10/0567; Y02E 60/10
See application file for complete search history.

(56) References Cited

U.S. PATENT DOCUMENTS 8,377,406 B1 * 2/2013 Singh ................. H01M 10/052
423/617
2017/0141432 A1 5/2017 Chen et al.
2018/0362343 A1 12/2018 Hormes et al.

FOREIGN PATENT DOCUMENTS

| CN | 106430129 A | 2/2017 |
| JP | 2017-010924 A | 8/2018 |
| JP | 2018-535181 A | 11/2018 |

OTHER PUBLICATIONS

Singh et al. "Bis(fluorosulphuryl)imide derivatives of zinc(II), cadmium(II), mercury(II) and their coordination complexes with oxygen and nitrogen donors" 1989, Indian Journal of Chemistry, vol. 28A, Oct. 1989, pp. 890-892 (Year: 1989).*

(Continued)

*Primary Examiner* — Wayne A Langel
*Assistant Examiner* — Syed T Iqbal
(74) *Attorney, Agent, or Firm* — Maschoff Brennan

(57) ABSTRACT

Provided is a compound represented by Formula (1) below.

$$M_a X_b Y_c \qquad (1)$$

(In Formula (1), M represents metal other than alkali metal, X represents $-N(SO_2F)_2$, Y represents a coordinating solvent, and a, b, and c are positive numbers.)

19 Claims, 5 Drawing Sheets

(56) References Cited

OTHER PUBLICATIONS

Singh, Sukhjinder et al., Indian Journal of Chemistry, 1989, 28A, 890-892p. 890-891, Table 1.
Vij, Ashwani et al., Indian Journal of Chemistry, 1993, 32A, 232-235p. 232-233, Table 1.
Vij, Ashwani et al., Bulletin De La Societe Chimique De France, 1989, 3, 331-333 p. 331-332, Table 1, Table 2.
Han, Sang-Don et al., "Electrolyte Solvation and Ionic Association: V. Acetonitrile-Lithium Bis(fluorosulfonyl)imide (LiFSI) Mixtures" Journal of The Electrochemical Society, 2014, 161(14), A2042-A2053.
Geysens, Pieter et al., The Journal of Physical Chemistry B, 2018, 122, 275-289.
Veryasov, Gleb et al., Dalton Transactions, 2016, 45, 2810-2813.
Yuki Yamada et., Electrochemistry, 2014, 82(12), 1085-1090.

* cited by examiner

BIS(FLUOROSULFONYL)IMIDE COMPOUND AND METHOD FOR PRODUCING SAME

TECHNICAL FIELD

The present invention relates to, e.g., a new bis(fluorosulfonyl)imide compound.

BACKGROUND ART

As, e.g., an electrolyte of a lithium ion secondary battery, lithium bis(fluorosulfonyl)imide has been utilized (Patent Document 1).

CITATION LIST

Patent Document

PATENT DOCUMENT 1: Japanese Unexamined Patent Publication No. 2017-10924

SUMMARY OF THE INVENTION

Technical Problem

An object of the present invention is to provide, e.g., a new bis(fluorosulfonyl)imide compound.

Solution to the Problem

As described above, alkali metal salt such as lithium bis(fluorosulfonyl)imide has been typically known as salt of bis(fluorosulfonyl)imide.

Meanwhile, the inventor(s) of the present invention has attempted to synthesize non-alkali metal salt of bis(fluorosulfonyl)imide. However, bis(fluorosulfonyl)imide has a counter-ion totally different in properties between an alkali metal ion and a non-alkali metal ion, and it has been found that even non-alkali metal salt cannot be stably obtained in some cases.

As a result of intensive study conducted by the inventor(s) of the present invention, the inventor(s) of the present invention has found that non-alkali metal salt of bis(fluorosulfonyl)imide containing a solvent (a solvent molecule) as a ligand can be relatively stably obtained through a particular method (step). The inventor(s) of the present invention has conducted further study to arrive at the present invention.

That is, the present invention relates to, e.g., the following aspects of the invention.

[1] A compound represented by Formula (1) below.

$$M_a X_b Y_c \qquad (1)$$

(In Formula (1), M represents metal (ion, cation) other than alkali metal, X represents —N(SO$_2$F)$_2$ (bis(fluorosulfonyl)imide (ion, anion)), Y represents a coordinating solvent (molecule), and a, b, and c are positive numbers.)

[2] The compound of [1], in which
the metal M includes at least one metal type (polyvalent metal) selected from group 2, 10 to 13 metals in a periodic table.

[3] The compound of [1] or [2], in which
the metal M includes group 2 metal in the periodic table.

[4] The compound of any one of [1] to [3], in which
the coordinating solvent Y includes at least one type selected from a nitrile-based solvent, a carbonate-based solvent, an ether-based solvent, an ester-based solvent, and a sulfone-based solvent.

[5] The compound of any one of [1] to [4], in which
the coordinating solvent Y includes at least one type selected from aliphatic nitrile, linear carbonate, cyclic carbonate, linear aliphatic ether, cyclic ether, linear ester, cyclic ester, and cyclic sulfone.

[6] The compound of any one of [1] to [5], in which
a water content is 5000 mass ppm or less.

[7] The compound of any one of [1] to [6], in which
a ratio among a, b, and c is a/b/c=1/2 to 3/1 to 8.

[8] The compound of [1], in which
the metal M is magnesium,
the coordinating solvent Y includes at least one type selected from acetonitrile, dimethyl carbonate, diethyl carbonate, ethyl methyl carbonate, ethylene carbonate, propylene carbonate, butylene carbonate, 1,2-dimethoxyethane, diethylene glycol dimethyl ether, triethylene glycol dimethyl ether, tetrahydrofuran, 2-methyltetrahydrofuran, 1,4-dioxane, 1,3-dioxolane, methyl acetate, ethyl acetate, ethyl propionate, propyl propionate, γ-butyrolactone, valerolactone, and sulfolane,
a water content is 5000 mass ppm or less, and
a ratio among a, b, and c is a/b/c=1/2 to 3/1 to 8.

[9] The method for producing the compound of any one of [1] to [8], including:
the reaction step of causing salt (a compound) of the metal M causing no water in reaction (reaction with bis(fluorosulfonyl)imide) and bis(fluorosulfonyl)imide to react with each other under the presence of a coordinating solvent.

[10] The production method of [9], in which
salt of the metal M is at least one type selected from halide, sulfate, nitrate, phosphate, chlorate, chromate, formate, acetate, and trifluoromethanesulfonate.

[11] The production method of claim [9] or [10], in which
0.3 to 1.5 equivalent of salt of the metal M is used for bis(fluorosulfonyl)imide.

[12] The production method of any one of claims [9] to [11], in which
at the reaction step, the reaction is made with a moisture amount of 5000 mass ppm or less in a reaction system.

[13] The production method of any one of [9] to [12], further including:
the ligand substitution step of obtaining, by means of a coordinating solvent Y1, a compound that the coordinating solvent Y is Y1 in Formula (1) at the reaction step and subsequently substituting at least part of the coordinating solvent Y1 with a coordinating solvent Y2.

[14] The production method of [13], in which
the coordinating solvent Y1 is a nitrile-based solvent, and the coordinating solvent Y2 is at least one type selected from a carbonate-based solvent, an ether-based solvent, an ester-based solvent, and a sulfone-based solvent.

[15] The production method of any one of [9] to [14], further including:
the step of recrystallizing the generated compound (a crude product) represented by Formula (1).

Advantages of the Invention

According to the present invention, e.g., a new bis(fluorosulfonyl)imide compound can be provided.

Such a compound of the present invention is non-alkali metal salt (e.g., magnesium salt) of bis(fluorosulfonyl)imide. Thus, such a compound is useful as a compound (e.g., an electrolyte or an additive) applicable for purposes relating to a non-alkali metal ion, such as a non-alkali metal ion battery (e.g., a magnesium ion battery).

Particularly, such a compound (e.g., magnesium salt) has properties such as a broad potential window, a high stability (e.g., thermal stability), a high conductivity, and the capability of non-alkali metal being intercalated/deintercalated, and can be suitably applied as, e.g., a compound for a non-alkali metal ion battery.

Note that the compound of the present invention contains the solvent (the coordinating solvent) as the ligand. Such a solvent is used as a solvent used for, e.g., an electrolytic solution so that this solvent can be directly used as, e.g., an electrolyte or an additive, for an electrolytic solution.

According to the present invention, the bis(fluorosulfonyl)imide compound as described above can be efficiently produced. In addition, a generated compound (e.g., a compound containing acetonitrile as a ligand) is relatively easily ligand-exchangeable. With such a compound, non-alkali metal salt of bis(fluorosulfonyl)imide containing a solvent as a ligand according to the intended use can be efficiently obtained.

DESCRIPTION OF EMBODIMENTS

Bis(fluorosulfonyl)imide Compound

Figure 1:
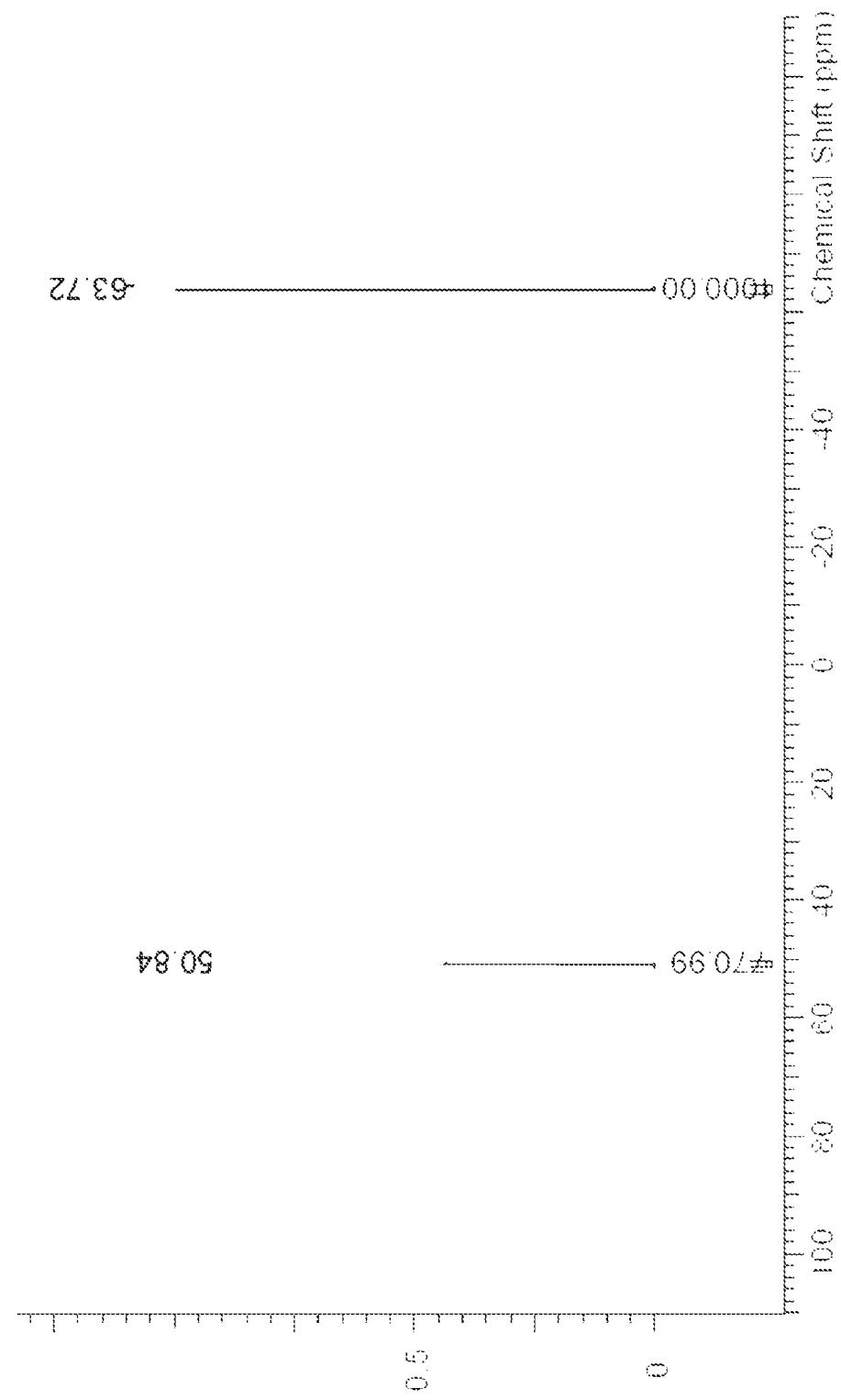
FIG. 1 is a chart obtained from $^{19}$F-NMR measurement of white powder obtained in Example 1.

A compound of the present invention is represented by Formula (1) below. In other words, the compound (sometimes referred to as, e.g., a "compound (1)") is non-alkali metal salt [salt of bis(fluorosulfonyl)imide (anion) and non-alkali metal (cation)] of bis(fluorosulfonyl)imide, containing a solvent (as a ligand).

$$M_aX_bY_c \quad (1)$$

(In Formula (1), M represents metal other than alkali metal, X represents —N(SO$_2$F)$_2$, and Y represents a coordinating solvent, and a, b, and c are positive numbers.)

In Formula (1), M represents metal (non-alkali metal) other than alkali metal. Examples of such metal M include typical metals [e.g., alkali earth metals or group 2 metals (e.g., beryllium, magnesium, calcium, strontium, and barium) in the periodic table, group 12 metals (e.g., zinc, cadmium, and mercury) in the periodic table, group 13 metals (e.g., aluminum, gallium, indium, and thallium) in the periodic table, group 14 metals (e.g., silicon, germanium, tin, and lead) in the periodic table, and group 15 metals (e.g., antimony and bismuth) in the periodic table] and transition metals [e.g., group 3 metals (e.g., scandium, yttrium, and lanthanoid) in the periodic table, group 4 metals (e.g., titanium, zirconium, and hafnium) in the periodic table, group 5 metals (vanadium, niobium, and tantalum) in the periodic table, group 6 metals (e.g., chromium, molybdenum, and tungsten) in the periodic table, group 7 metals (e.g., manganese) in the periodic table, group 8 metals (e.g., iron and ruthenium) in the periodic table, group 9 metals (e.g., cobalt, rhodium, and iridium) in the periodic table, group 10 metals (e.g., nickel, palladium, and platinum) in the periodic table, and group 11 metals (e.g., copper, silver, and gold) in the periodic table].

The metal M may be contained alone or in combination of two or more types in the compound represented by Formula (1). Note that the metal M may contain alkali metal as long as the metal M contains non-alkali metal, but normally contains no alkali metal in many cases.

Of these metals, e.g., the group 2 metals, the group 10 metals, the group 11 metals, the group 12 metals, the group 13 metals, and the group 14 metals in the periodic table are representative metals. The group 2 metals, the group 10 metals, the group 11 metals, the group 13 metals, and the group 14 metals in the periodic table are preferred, the group 2 metals (e.g., calcium and magnesium) and the group 13 metals (e.g., aluminum) in the periodic table are more preferred, and magnesium is much more preferred.

Thus, the metal M may contain at least these metals (e.g., at least one type selected from the group 2 metals, the group 10 metals, the group 11 metals, the group 12 metals, the group 3 metals, and the group 14 metals in the periodic table, the group 2 metals in the periodic table).

Note that the metal (non-alkali metal) M may be polyvalent metal (ion) in Formula (1). The valence of the metal M is not particularly limited and can be selected according to the type of metal M, and for example, may be divalent (2+) to octavalent (8+), preferably divalent to hexavalent, more preferably divalent to tetravalent or divalent or trivalent (particularly, divalent).

Specific examples of the metal (cation) include divalent metal cations (e.g., Mg$^{2+}$, Ca$^{2+}$, Zn$^{2+}$, Pd$^{2+}$, Sn$^{2+}$, Hg$^{2+}$, Rh$^{2+}$, Cu$^{2+}$, Be$^{2+}$, Sr$^{2+}$, and Ba$^{2+}$) and trivalent metal cations (e.g., Al$^{3+}$ and Ga$^{3+}$). Of these metals, alkali earth metal cations and Al$^{3+}$ are preferred, Mg$^{2+}$, Ca$^{2+}$, and Al$^{3+}$ are more preferred because these metals have small ion radiuses and are easily utilized for batteries etc., and Mg$^{2+}$ is much more preferred.

In Formula (1), X represents —N(SO$_2$F)$_2$ (sometime referred to as FSI). It can be said that X is bis(fluorosulfonyl)imide (anion) (the following formula).

[Chemical Formula 1]

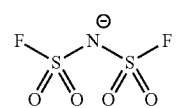

In Formula (1), Y represents the solvent (a molecule). Such a solvent (the coordinating solvent) is not particularly limited as long as the solvent exhibits coordinating properties [or can be a ligand (the ligand of the metal M)]. Examples of the solvent include heteroatom-containing (hetero element-containing) solvents (heteroatom-containing non-aqueous solvents) such as nitrogen-containing solvents, oxygen-containing solvents, and sulfur-containing solvents and water.

Examples of the nitrogen-containing solvent include nitrile-based solvents, amide-based solvents, nitro-based solvents (e.g., nitromethane), amine-based solvents [e.g., linear amines (e.g., aliphatic amines such as methylamine and dimethylamine) and cyclic amines (e.g., piperidine)], and aromatic solvents [e.g., pyridine-based solvents (e.g., pyridine)].

Examples of the nitrile-based solvent include aliphatic nitriles [e.g., cyanoalkanes (e.g., mono- or dicyanoalkanes) such as acetonitrile, propionitrile, butyronitrile, isobutyronitrile, valeronitrile, methoxypropionitrile, glutaronitrile, adiponitrile, and 2-methylglutaronitrile, preferably mono- or dicyano $C_{1-4}$ alkanes] and aromatic nitriles (e.g., benzonitrile and tolunitrile).

Examples of the amide-based solvent include linear amides [e.g., linear aliphatic amides (e.g., alkanoic acid amides such as dimethylformamide and dimethylacetamide)] and cyclic amides (or lactam such as N-methylpyrrolidone).

Examples of the oxygen-containing solvent include carbonate-based solvents, ether-based solvents, ester-based solvents, ketone-based solvents, and alcohol-based solvents [e.g., linear alcohols (e.g., alkanols such as methanol and ethanol) and cyclic alcohols (e.g., cyclohexanol)].

Examples of the carbonate-based solvent include linear carbonates [e.g., dialkyl carbonates (e.g., di-$C_{1-4}$ alkyl carbonates such as dimethyl carbonate (DMC), ethyl methyl carbonate (EMC), and diethyl carbonate (DEC), preferably di-$C_{1-2}$ alkyl carbonates), alkylaryl carbonates (e.g., $C_{1-4}$ alkyl phenyl carbonates such as methyl phenyl carbonate), and diaryl carbonates (e.g., diphenyl carbonate)] and cyclic carbonates {e.g., saturated cyclic carbonates [e.g., alkylene carbonates (e.g., $C_{2-6}$ alkylene carbonate, preferably $C_{2-4}$ alkylene carbonate) such as ethylene carbonate, propylene carbonate, 2,3-dimethyl ethylene carbonate, and 1,2-butylene carbonate, and erythritan carbonate], unsaturated cyclic carbonates (e.g., alkenylene carbonates such as vinylene carbonate, methyl vinylene carbonate, and ethyl vinylene carbonate; 2-vinyl ethylene carbonate), and fluorine-containing cyclic carbonates (e.g., fluoroethylene carbonate, 4,5-difluoroethylene carbonate, and trifluoropropene carbonate)}.

Examples of the ether-based solvent include linear ethers {e.g., linear aliphatic ethers [e.g., alkanediol dialkyl ethers (e.g., $C_{2-4}$ alkanediol di-$C_{1-4}$ alkyl ethers such as 1,2-dimethoxyethane (ethylene glycol dimethyl ether) and ethylene glycol diethyl ether) and polyalkanediol dialkyl ethers (e.g., di- to tetra-$C_{2-4}$ alkanediol di-$C_{1-4}$ alkyl ethers such as triethylene glycol dimethyl ether and tetraethylene glycol dimethyl ether)]} and cyclic ethers [e.g., tetrahydrofurans (e.g., tetrahydrofuran, 2-methyltetrahydrofuran, and 2,6-dimethyltetrahydrofuran), tetrahydropyrans (e.g., tetrahydropyran), dioxanes (e.g., 1,4-dioxane), dioxolanes (e.g., 1,3-dioxolane), and crown ether].

Examples of the ester-based solvent include linear esters {e.g., aliphatic esters [e.g., alkanoic acid esters (e.g., $C_{1-5}$ alkanoic acid $C_{1-4}$ alkyl esters) such as methyl acetate, ethyl acetate, ethyl propionate, and propyl propionate] and aromatic esters (e.g., methyl benzoate and ethyl benzoate)} and cyclic esters [or lactones such as γ-butyrolactone and valerolactones (γ-valerolactone and δ-valerolactone)].

Examples of the ketone-based solvent include linear ketones (e.g., dialkylketones such as acetone, methyl ethyl ketone, and methyl isopropyl ketone) and cyclic ketones [e.g., cycloalkanones (e.g., cyclohexanone) and heterocyclic ketones (e.g., 1,3-dimethyl-2-imidazolidinone, 1,3-dimethyl-3,4,5,6-tetrahydro-2(1H)-pyrimidinone, and 3-methyl-2-oxazolidinone)].

Examples of the sulfur-containing solvent include sulfones (sulfone-based solvents) such as linear sulfones (or linear sulfone-based solvents such as dialkyl sulfones including dimethyl sulfone, ethyl methyl sulfone, and diethyl sulfone) and cyclic sulfones [e.g., sulfolanes (or sulfolane-based solvents such as sulfolane, 3-methylsulfolane, and 2,4-dimethylsulfolane)].

The solvent Y may be contained alone or in combination of two or more types in the compound represented by Formula (1).

Of these solvents, e.g., a nitrile-based solvent, a carbonate-based solvent, an ether-based solvent, an ester-based solvent, and a sulfone-based solvent are preferred. Of these solvents, aliphatic nitrile, linear carbonate, cyclic carbonate, linear aliphatic ether, cyclic ether, linear ester (e.g., aliphatic ester such as $C_{1-5}$ alkanoic acid $C_{1-4}$ alkyl ester), cyclic ester, and cyclic sulfone (e.g., sulfolanes) are preferred. More representative solvents include, for example, acetonitrile, dimethyl carbonate, diethyl carbonate, ethyl methyl carbonate, ethylene carbonate, propylene carbonate, butylene carbonate, 1,2-dimethoxyethane, diethylene glycol dimethyl ether, triethylene glycol dimethyl ether, tetrahydrofuran, 2-methyltetrahydrofuran, 1,4-dioxane, 1,3-dioxolane, methyl acetate, ethyl acetate, ethyl propionate, propyl propionate, γ-butyrolactone, valerolactone, and sulfolane.

These solvents are suitable because stable coordination structures thereof can be easily provided. In many cases, these solvents are solvents which can be used (or can be included) in, e.g., a battery or an electrolyte. With these solvents, the compound represented by Formula (1) can be directly used in, e.g., the electrolyte.

The solvent such as acetonitrile is relatively easily substituted as described later, and a compound having such a solvent Y can be suitably used as a compound for obtaining a compound having a different solvent as Y.

Thus, the solvent Y may contain at least the following solvent [e.g., at least one type selected from nitrile-based solvents (e.g., aliphatic nitrile), carbonate-based solvents (e.g., linear carbonate and cyclic carbonate), ether-based solvents (e.g., linear aliphatic ether and cyclic ether), and ester-based solvents].

Further, the compound represented by Formula (1) or the solvent Y may contain at least an aprotic solvent (e.g., solvents other than water, alcohol-based solvents, and amine-based solvents), and may contain (substantially) no protic solvent (e.g., water). Note that in a case where the compound represented by Formula (1) contains the protic solvent, the form of such a contained solvent is not particularly limited and the solvent may be contained as (part of) the solvent Y, for example.

For example, in the compound represented by Formula (1), the proportion of water may be 20000 mass ppm or less (e.g., 10000 mass ppm or less), preferably 5000 mass ppm or less (e.g., 3000 mass ppm or less), more preferably 2000 mass ppm or less, and much more preferably 1500 mass ppm or less, or may be 1000 mass ppm or less, 500 mass ppm or less, 250 mass ppm or less, 100 mass ppm or less, 50 mass ppm or less, or 0 mass ppm (or a detection limit).

In the solvent Y, the proportion of water may be 20000 mass ppm or less (e.g., 10000 mass ppm or less), preferably 5000 mass ppm or less (e.g., 3000 mass ppm or less), more preferably 2000 mass ppm or less, and much more preferably 1500 mass ppm or less, or may be 1000 mass ppm or less, 500 mass ppm or less, 250 mass ppm or less, 100 mass ppm or less, 50 mass ppm or less, or 0 mass ppm (or a detection limit).

Note that a moisture amount can be measured by a Karl-Fischer method, for example.

With a compound having a small moisture amount as described above, reaction such as hydrolysis is less likely to occur, and a high stability (hydrolysis stability) is easily carried as a compound. With this level of moisture amount, removal can be stably performed if such removal is necessary. Such a compound is suitable because the compound is easily used as, e.g., an electrolyte.

In Formula (1), any of a, b, and c is the positive number. That is, the compound represented by Formula (1) inevitably contains the metal M, X, and the solvent Y, and the ratio (the composition ratio) of these substances in the compound can be represented as a/b/c.

For example, when a is 1 (i.e., with respect to one atom of the metal M) in Formula (1), b may be, depending on, e.g., the types of metal M and solvent Y, 0.1 or more (e.g., 0.1 to 10), preferably 0.3 or more (e.g., 0.3 to 9), and more preferably 0.5 or more (e.g., 0.5 to 8), or may be normally 1 or more [e.g., 1 to 5, 1.2 or more (e.g., 1.2 to 4.5), 1.5 or more (e.g., 1.5 to 4), 1.7 or more (e.g., 1.7 to 3.5), 2 or more (e.g., 2 to 2.5), or 2].

For example, when a is 1 in Formula (1), c may be, depending on, e.g., the types of metal M and solvent Y, 0.1 or more (e.g., 0.1 to 25), preferably 0.2 or more (e.g., 0.2 to 20), and more preferably 0.3 or more (e.g., 0.3 to 18), or may be normally 0.4 or more [e.g., 0.4 to 15, 0.7 or more (e.g., 0.7 to 12), 0.8 or more (e.g., 0.8 to 10), 1 or more (e.g., 1 to 8), 1.5 or more (e.g., 1.8 to 8), or 2 or more (e.g., 2 to 7.5)].

For example, in a more specific form, a/b/c may be, in Formula (1), 1/0.1 to 10 (e.g., 0.5 to 8)/0.1 to 25 (e.g., 0.2 to 20), preferably 1/1 to 5 (e.g., 1.2 to 4.5)/0.3 to 18 (e.g., 0.4 to 15), more preferably 1/1.5 to 4 (e.g., 1.7 to 3.5)/0.7 to 12 (e.g., 0.8 to 10), and much more preferably 1/2 to 3 (e.g., 2 to 2.5)/1 to 8 (e.g., 2 to 7.5).

The method for producing the compound represented by Formula (1) is not particularly limited, and such a compound can be efficiently produced by a later-described method.

[Production Method]

The present invention also includes the method for producing the bis(fluorosulfonyl)imide compound. Particularly, such a compound may be the compound (the bis(fluorosulfonyl)imide compound) described above as an example.

Such a producing method of the present invention includes at least the reaction step of causing metal salt (or a metal compound) and bis(fluorosulfonyl)imide to react with each other under the presence of a coordinating solvent (e.g., a coordinating solvent Y).

At the reaction step, the coordinating solvent includes, for example, the coordinating solvent Y described above as an example, and the preferred form etc. thereof are similar to those described above.

At the reaction step, metal salt (or the metal compound) is not particularly limited as long as metal salt can react with bis(fluorosulfonyl)imide. However, metal salt causing no water in reaction (reaction with bis(fluorosulfonyl)imide) is preferred.

Specific examples of metal salt include salt (a compound) of metal (the metal M) described above as an example, such as halides (or halogenated hydrogen salt), inorganic acid salts (e.g., oxo acid salts such as sulfate, nitrate, phosphate, chlorate, and chromate), and organic acid salts [e.g., carboxylates (e.g., alkanoates such as formate and acetate) and sulfonates (e.g., trifluoromethanesulfonate)]. Of these substances, halide may be suitably used.

In halide, halogen is not particularly limited, but may be, e.g., chlorine (atom), bromine (atom), or iodine (atom) or may be particularly chlorine.

Specific examples of metal halide include halogenated alkali earth metals [e.g., magnesium halides such as magnesium chloride ($MgCl_2$)].

It can be said that bis(fluorosulfonyl)imide is a compound (the following formula) represented by $HN(SO_2F)_2$ (also sometimes referred to as HFSI).

[Chemical Formula 2]

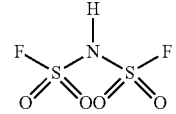

Note that as described above, the bis(fluorosulfonyl)imide compound (the compound (1) described above) may be a compound with a small amount of protic solvent as the coordinating solvent, particularly water. In the case of obtaining such a compound, the coordinating solvent, metal salt, and/or bis(fluorosulfonyl)imide used as raw materials may also have small solvent contents as described above.

The content of water in such a coordinating solvent may be, for example, 20000 mass ppm or less (e.g., 10000 mass ppm or less), preferably 5000 mass ppm or less (e.g., 3000 mass ppm or less), more preferably 2000 mass ppm or less, and much more preferably 1500 mass ppm or less, or may be 1000 mass ppm or less, 500 mass ppm or less, 250 mass ppm or less, 100 mass ppm or less, 50 mass ppm or less, or 0 mass ppm (or a detection limit).

The content of water (including the case of containing water as, e.g., hydrate) in metal salt may be, for example, 20000 mass ppm or less (e.g., 10000 mass ppm or less), preferably 5000 mass ppm or less (e.g., 3000 mass ppm or less), more preferably 2000 mass ppm or less, and much more preferably 1500 mass ppm or less, or may be 1000 mass ppm or less, 500 mass ppm or less, 250 mass ppm or less, 100 mass ppm or less, 50 mass ppm or less, or 0 mass ppm (or a detection limit).

The content of water in bis(fluorosulfonyl)imide may be, for example, 20000 mass ppm or less (e.g., 10000 mass ppm or less), preferably 5000 mass ppm or less (e.g., 3000 mass ppm or less), more preferably 2000 mass ppm or less, and much more preferably 1500 mass ppm or less, or may be 1000 mass ppm or less, 500 mass ppm or less, 250 mass ppm or less, 100 mass ppm or less, 50 mass ppm or less, or 0 mass ppm (or a detection limit).

Note that the reaction step may be performed under the presence of an appropriate medium [e.g., a solvent which is not a coordinating solvent and an inactive (unreactive) solvent in reaction (the reaction between metal salt and the coordinating solvent)] or may be performed without such a medium. In the present invention, the solvent (the coordinating solvent) can be used as a reaction component, and therefore, the reaction can efficiently progress without the need for adding a solvent.

At the reaction step, the proportion (use ratio) of each component (the coordinating solvent, bis(fluorosulfonyl)imide, and metal salt) can be selected as necessary according to, e.g., an intended type of bis(fluorosulfonyl)imide compound.

At the reaction step, the proportions of bis(fluorosulfonyl)imide and metal salt (e.g., salt of the metal M, such as metal halide M) may be, for example, 0.05 equivalent or more (e.g., 0.1 equivalent or more), preferably 0.2 equivalent or more (e.g., 0.3 equivalent or more), and more preferably 0.4 equivalent or more (e.g., 0.5 equivalent or more) of metal salt with respect to bis(fluorosulfonyl)imide, or may be 0.6 equivalent or more (e.g., 0.7 equivalent or more, 0.8 equivalent or more, 0.9 equivalent or more, 0.95 equivalent or more, 1 equivalent or more, or 1.01 equivalent or more).

Particularly, the proportions of bis(fluorosulfonyl)imide and metal salt may be, for example, 2 equivalent or less (e.g., 1.8 equivalent or less), preferably 1.6 equivalent or less (e.g., 1.5 equivalent or less), and more preferably 1.4 equivalent or less (e.g., 1.3 equivalent or less) of metal salt with respect to bis(fluorosulfonyl)imide, or may be 1.2 equivalent or less (e.g., 1.15 equivalent or less, 1.1 equivalent or less, or 1 equivalent or less).

A relatively-small amount of bis(fluorosulfonyl)imide is used or a large excess of bis(fluorosulfonyl)imide is not used as described above [e.g., use with a proportion of 2 equivalent or less (e.g., 0.8 to 2 equivalent), 1.5 equivalent or less, or 1.2 equivalent or less (e.g., 0.8 to 1.2 equivalent or 0.9 to 1.15 equivalent)], and therefore, an intended object can be easily efficiently obtained.

Note that the "equivalent" can be selected according to the valence of metal (metal salt), and in the case of divalent metal (e.g., magnesium), "1 equivalent" with respect to bis(fluorosulfonyl)imide (monovalent) means "0.5 mol" with respect to 1 mol of bis(fluorosulfonyl)imide, for example.

At the reaction step, the proportion (use ratio) of the solvent is not particularly limited, and can be selected according to, e.g., the amount (proportion) of solvent contained in the intended object. For example, such a proportion may be, with respect to metal salt, 0.05 equivalent or more (e.g., 0.1 equivalent or more), preferably 0.2 equivalent or more (e.g., 0.3 equivalent or more), and more preferably 0.4 equivalent or more (e.g., 0.5 equivalent or more), or may be 0.6 equivalent or more (e.g., 0.7 equivalent or more, 0.8 equivalent or more, 0.9 equivalent or more, 0.95 equivalent or more, 1 equivalent or more, 1.5 equivalent or more, 2 equivalent or more, 3 equivalent or more, or 5 equivalent or more).

Note that the upper limit of the proportion of the solvent with respect to metal salt is not particularly limited and may be a large excess or 1000 equivalent, 500 equivalent, 300 equivalent, 200 equivalent, or 100 equivalent.

Note that as described above, the bis(fluorosulfonyl)imide compound (the compound (1) described above) may be the compound with a small amount of protic solvent, particularly water. For obtaining such a compound, the amount (moisture amount) water in a reaction system is preferably relatively small, and the reaction may be made particularly with (substantially) no water.

In this case, the moisture amount in the reaction system [or a reaction liquid mixture or the total amount of the coordinating solvent, bis(fluorosulfonyl)imide, and metal salt] may be, for example, specifically 20000 mass ppm or less (e.g., 10000 mass ppm or less), preferably 5000 mass ppm or less (e.g., 3000 mass ppm or less), more preferably 2000 mass ppm or less, and much more preferably 1500 mass ppm or less, or may be 1000 mass ppm or less, 500 mass ppm or less, 250 mass ppm or less, 100 mass ppm or less, 50 mass ppm or less, or 0 mass ppm (or a detection limit).

Note that each component may be all charged into the reaction system (a reactor) at the initial stage of the reaction step, or may be charged (added) in a stepwise manner. In this case, the order, timing, and speed of addition of each component can be selected as necessary. For example, HFSI may be added to a system including metal halide and the coordinating solvent.

At the reaction step, a temperature (a reaction temperature) is not particularly limited, and may be under any of a heated condition, a room temperature condition, and a cooled condition. Particularly, the temperature may be 100° C. or less (e.g., 80° C. or less or 60° C. or less), preferably 50° C. or less (e.g., 30° C. or less), and more preferably 20° C. or less (e.g., 10° C. or less), or may be 0° C. or less (e.g., –10° C. or less or –20° C. or less). The lower limit of the reaction temperature is not particularly limited, and may be –100° C., –80° C., –70° C., –60° C., –40° C., –20° C., or 0° C., for example. A representative temperature may be about –20° C. to 100° C. (e.g., 0° C. to 60° C.).

The reaction may be performed under stirring. Moreover, the reaction is preferably performed under atmosphere with a low dew point. In this case, the dew point may be, for example, 0° C. or less, more preferably –10° C. or less, –20° C. or less, much more preferably –30° C. or less, or still much more preferably –50° C. or less. The reaction may be performed under inert atmosphere (e.g., in nitrogen, helium, or argon).

Note that acid might be normally generated due to the reaction. Such acid might decompose a product, and for this reason, the reaction is preferably made while removing the generated acid. The method for removing the generated acid is not particularly limited, and may be selected according to, e.g., the type of generated acid. For example, in a case where hydrogen halide is generated, the method for removing such hydrogen halide by flow with atmospheric gas, bubbling with atmospheric gas, or alkaline trap is preferred.

A reaction time can be selected as necessary according to, e.g., the type or amount of each component, and is not particularly limited. For example, the reaction time may be 0.1 hours or more (e.g., 0.5 hours or more), preferably 3 hours or more, and more preferably 5 hours or more. A representative reaction time may be about 0.1 hours to 48 hours (e.g., 0.1 hours to 24 hours).

The product (e.g., the compound (1) described above) is obtained through the above-described reaction step. The product may be purified and recovered from the reaction liquid mixture after the reaction (after the reaction step), as necessary.

A purifying method is not particularly limited, and a general method (e.g., filtration, distilling, condensation, or recrystallization) can be utilized.

Particularly, the reaction often uses an excess of solvent (coordinating solvent), and for this reason, the reaction liquid mixture may be, for example, condensed for the purpose of removing the solvent (the coordinating solvent). Purification (e.g., condensation) may be performed under an increased temperature or a reduced pressure. In this case, condensation may be performed with a relatively-gentle temperature or pressure. Purification (condensation) is performed under such a condition so that, e.g., decomposition of the product can be reduced as much as possible and can be efficiently obtained (recovered).

For example, the temperature in purification (e.g., condensation) may be 100° C. or less, preferably 90° C. or less (e.g., 85° C. or less), more preferably 80° C. or less (e.g., 75° C. or less), and much more preferably 70° C. or less (e.g., 65° C. or less). The lower limit of the temperature is not particularly limited, and can be set as necessary within a condensable temperature range (e.g., a room temperature (e.g., 35° C., 30° C., 20° C., or 15° C.), or 10° C., 0° C., –10° C., or –20° C.). A representative temperature in purification (e.g., condensation) may be about 0 to 100° C. (e.g., 20° C. to 60° C.).

In a case where the pressure is reduced in purification (e.g., condensation), such a pressure (the degree of pressure reduction) can be selected from a range of an atmospheric pressure or less, and for example, may be 900 hPa or less, 800 hPa or less, 700 hPa or less, 600 hPa or less, 500 hPa or less, 400 hPa or less, 300 hPa or less, 200 hPa or less, 150 hPa or less, 120 hPa or less, 100 hPa or less, or 80 hPa or less. The lower limit of the pressure may be, for example, 3 hPa, 5 hPa, 10 hPa, 20 hPa, 30 hPa, 40 hPa, 50 hPa, or 60 hPa.

The product (e.g., the compound (1) described above) contains a coordinating solvent (as a ligand) corresponding to the coordinating solvent used. Such a coordinating solvent may be substituted with another coordinating solvent, and in this manner, another product (e.g., a compound (1) with a different ligand or composition thereof) may be obtained.

Thus, the producing method of the present invention may include the step (the ligand substitution step) of substituting the coordinating solvent after the reaction step.

It can be said that such a method is a method including the ligand substitution step of obtaining, by means of a coordinating solvent Y1, a product (sometimes referred to as, e.g., a compound, a first compound, or a first product) that the coordinating solvent Y is Y1 in Formula (1) at the reaction step and subsequently substituting at least part of the coordinating solvent Y1 with a coordinating solvent Y2.

A combination of the coordinating solvent Y1 and the coordinating solvent Y2 is not particularly limited, and it may only be required that these solvents are different solvents. Particularly, in a case where the coordinating solvent Y1 is, e.g., a nitrile-based solvent (e.g., acetonitrile), substitution with the coordinating solvent Y2 relatively easily progresses.

Specific examples of the combination include, but not limited to, combinations of nitrile-based solvents (aliphatic nitrile and acetonitrile) as the coordinating solvent Y1 and non-nitrile-based solvents (e.g., at least one type selected from carbonate-based solvents, ether-based solvents, ester-based solvents, and sulfone-based solvents) as the coordinating solvent Y2.

At the ligand substitution step, at least part of the coordinating solvent Y1 in the first compound is substituted with the coordinating solvent Y2 (the solvent different from the coordinating solvent Y1). A substitution method is not particularly limited, and the first compound and the coordinating solvent Y2 may contact each other (e.g., mixed with each other), for example.

At the ligand substitution step, the amount (the amount of coordinating solvent Y2 which is to contact 1 mol of the first compound (or Y1)) of coordinating solvent Y2 is not particularly limited, but may be, for example, 0.1 mol or more (e.g., 0.2 mol or more), 0.5 mol or more (e.g., 0.7 mol or more), 1 mol or more (e.g., 1.2 mol or more), 1.5 mol or more (e.g., 1.8 mol or more), or 2 mol or more with respect to the first compound.

The ligand substitution step may be performed under any of a heated condition, a room temperature condition, or a cooled condition. The ligand substitution step may be performed under stirring. The ligand substitution step may be preferably performed under low-dew-point atmosphere, and may be performed under inert atmosphere (e.g., in nitrogen, helium, or argon). These conditions may be selected from a range similar to that described above.

A time for which the first compound and the coordinating solvent contact each other at the ligand substitution step can be selected as necessary according to, e.g., the type or amount of each component, and is not particularly limited. For example, such a time may be 1 minute or more, preferably 10 minutes or more, more preferably 30 minutes or more, and much more preferably 1 hour or more.

Note that at the ligand substitution step, a pressure may be reduced during or after contact. By pressure reduction, substitution of the coordinating solvent and removal (purification) of the deintercalated coordinating solvent can be efficiently performed.

From this point of view, the boiling point Y1 of the coordinating solvent Y1 is suitably lower than or equal to the boiling point Y2 of the coordinating solvent Y2, or is suitably not too high even in a case where the boiling point Y1 is higher than the boiling point Y2. For example, a difference (Y2−Y1) between the boiling point Y2 and the boiling point Y1 may be −30° C. or more, −20° C. or more, −10° C. or more, −5° C. or more, −3° C. or more, or 0° C. or more.

Note that in a case where the pressure is reduced, the pressure (the degree of pressure reduction) may be selected from a range similar to that described above.

A product (sometimes referred to as, e.g., a compound, a second compound, or a second product) that at least part of the coordinating solvent Y1 is substituted with the coordinating solvent Y2 is obtained through the ligand substitution step. The second product may be purified and recovered from a mixture (a reaction mixture) after the ligand substitution step, as necessary. As a purification method, a method similar to that described above may be selected.

At any of the reaction step and the ligand substitution step, the product (the first product, the second product, or a crude product) may be purified by a method such as recrystallization, as necessary. By such purification, a high-purity intended compound (the first compound or the second compound) can be efficiently obtained.

A recrystallization method is not particularly limited, and a general method can be utilized. For example, recrystallization may be performed in the same coordinating solvent Y as the coordinating solvent Y forming the product.

EXAMPLES

Hereinafter, the present invention will be more specifically described with reference to examples, but the present invention is not limited to the examples below.

Note that various analysis/measurement methods performed in the present examples are as follows.

[ICP Emission Spectrochemical Analysis Method]

Using a multitype ICP emission spectrochemical analysis apparatus ("ICPE-9000" manufactured by Shimadzu Corporation), a magnesium substance contained in a product was analyzed.

[NMR Measurement]

Using "Unity Plus—400" manufactured by Varian Medical Systems, $^1$H-NMR and $^{19}$F-NMR were measured (a deuterated solvent: dimethyl sulfoxide, an internal standard material: trifluorotoluene or benzenesulfonyl fluoride, the number of times of integration: 16 ($^1$H-NMR), 64 ($^{19}$F-NMR)).

[IR Measurement]

IR measurement was performed using "Scimitar 2000 FT-IR" manufactured by Varian Medical Systems and "MIRacle ATR" manufactured by PIKE Technologies.

[Karl-Fischer (KF) Measurement]

KF measurement was performed using "AQ-2000" manufactured by HIRANUMA, and the amount of moisture contained in the product was analyzed.

[Raman Measurement]

Raman measurement was performed using "NRS-3100" manufactured by JASCO Corporation.

Example 1

Synthesis of $Mg(FSI)_2(MeCN)_2$

A reaction container of 100 ml to which a stirrer, a thermometer, and a dripping apparatus are attached was placed under a nitrogen gas stream, and 2.09 g (22.0 mmol, 1.00 eq.) of magnesium chloride ($MgCl_2$) and 30.0 ml (574 mmol, 26.1 eq., a moisture amount of 7.8 mass ppm) of super dehydrated acetonitrile (MeCN) were added and was cooled to 4° C. in an ice bath.

A solution mixture of 7.23 g (39.9 mmol, 1.81 eq.) of bis(fluorosulfonyl)imide and 15.0 ml (287 mmol, 13.0 eq., a moisture amount of 7.8 mass ppm) of super dehydrated acetonitrile was added to the dripping apparatus, and was slowly dripped for 25 minutes.

After the end of dripping, the resultant is continuously stirred for 12 hours while the temperature thereof is being slowly increased. A clouded reaction mixture was obtained. Suction filtration was performed using a Kiriyama funnel. A white solid was filtered, and thereafter, a resultant clear colorless solution was pressure-reduced and condensed using an evaporator (55° C., 70 hPa). In this manner, 12.79 g of a white powdery solid was obtained.

Figure 2:
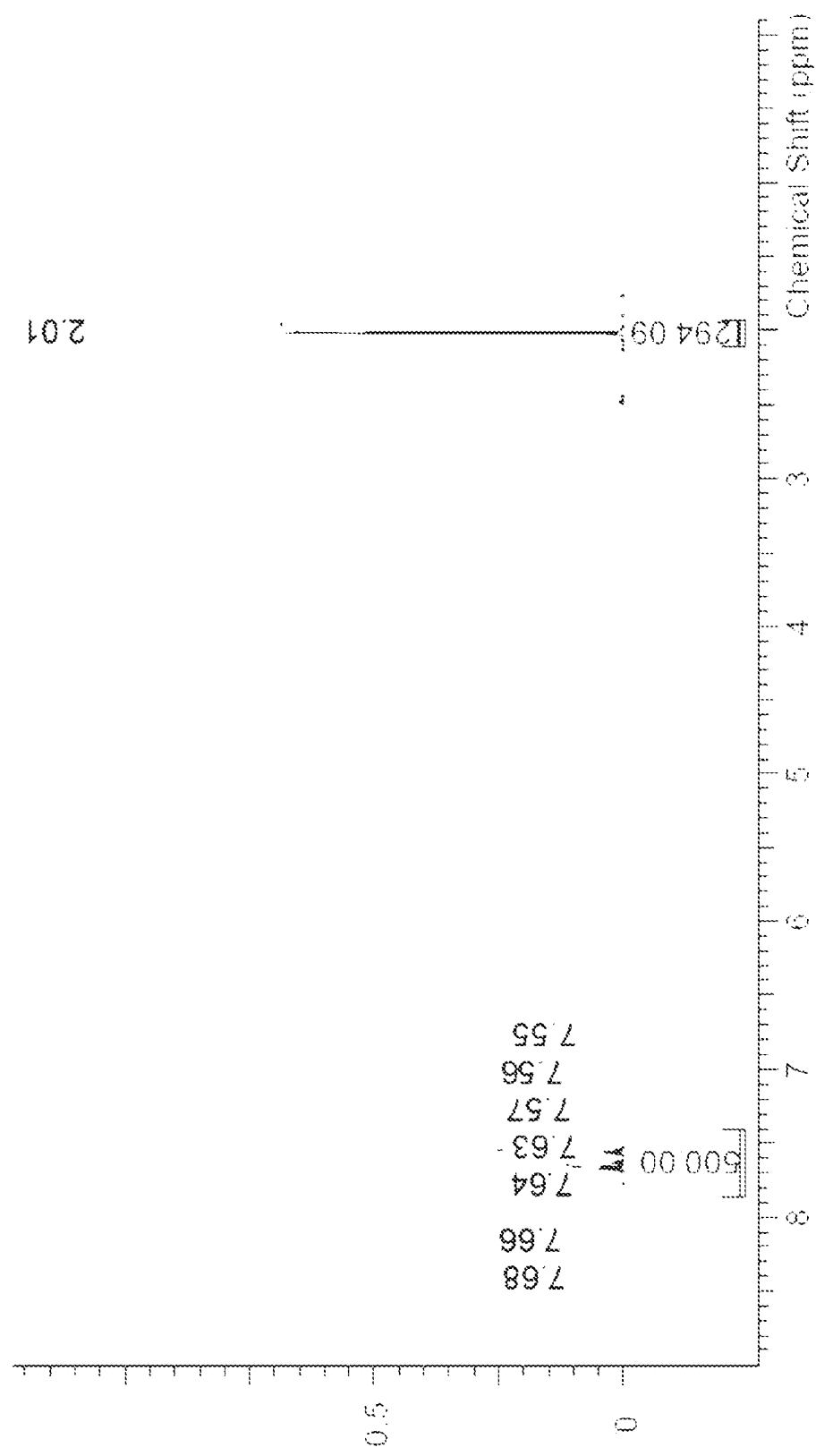
FIG. 2 is a chart obtained from $^{1}$H-NMR measurement of the white powder obtained in Example 1.

As a result of IR measurement for the resultant white powder, stretching vibration derived from FSI was observed at 1110 $cm^{-1}$ and 1180 $cm^{-1}$. Moreover, stretching vibration derived from $SO_2$ was observed at 1365 $cm^{-1}$, and the presence of an FSI structure was confirmed. In $^{19}F$-NMR measurement for the white powder, only the peak of the product (derived from FSI) was confirmed at δ=55.4 ppm (FIG. 1). In FIG. 1, a peak confirmed at −63.72 ppm is the peak of trifluorotoluene added as an internal standard. Further, as a result of $^1H$-NMR measurement (using the same sample as an NMR sample in $^{19}F$-NMR measurement), only the peak of acetonitrile was confirmed at 2.01 ppm (FIG. 2). In FIG. 2, peaks confirmed at 7.5 to 7.7 ppm are the peaks of trifluorotoluene added as the internal standard. Of these two types of NMR results, an integrated value ratio between the peak of the FSI-derived product measured from $^{19}F$-NMR and the peak of acetonitrile measured from $^1H$-NMR with respect to the internal standard shows that an existence value ratio between FSI and acetonitrile is 2:7 in terms of a molar ratio. In ICP (Shimadzu ICPE-9000), only 3.6 mass % of magnesium was detected.

These measurement results show that an existence value ratio among magnesium, bis(fluorosulfonyl)imide, and acetonitrile is 1:2:7. Thus, it was confirmed that the product is $Mg(FSI)_2(MeCN)_7$ (a yield of 98%).

Subsequently, in $^{19}F$-NMR measurement, in a case where trifluorotoluene was used as the internal standard, a substance (a substance whose peak was confirmed at 55.9 ppm when the peak position of benzenesulfonyl fluoride was 68.9 ppm in a case where benzenesulfonyl fluoride was used as an internal standard) whose peak was confirmed at 50.8 ppm was taken as being generated by $Mg(FSI)_2$, and the coordination number of such a solvent was calculated using a method similar to that described above only from $^{19}F$-NMR and $^1H$-NMR. Moreover, as a result of KF measurement, the amount of moisture in the product was 1082 mass ppm.

Example 2

Synthesis of $Mg(FSI)_2(MeCN)_6$

An excess of super dehydrated acetonitrile (MeCN) (a moisture amount of 7.8 mass ppm) was added to the product obtained in Example 1. The resultant was heated to 50° C., and thereafter, was cooled overnight in a freezer at −10° C. A white crystal was obtained.

As a result of $^{19}F$-NMR measurement for the resultant product (the white crystal), only a single peak derived from $Mg(FSI)_2$ was confirmed at δ=50.8 ppm. As a result of 41-NMR measurement, a single peak derived from acetonitrile was confirmed at δ=2.05 ppm. From an integrated value ratio with respect to an internal standard (using trifluorotoluene) in these NMR results, it has been confirmed that the resultant product is $Mg(FSI)_2(MeCN)_6$. As a result of KF measurement, the amount of moisture in the product was 455 mass ppm.

Figure 3:
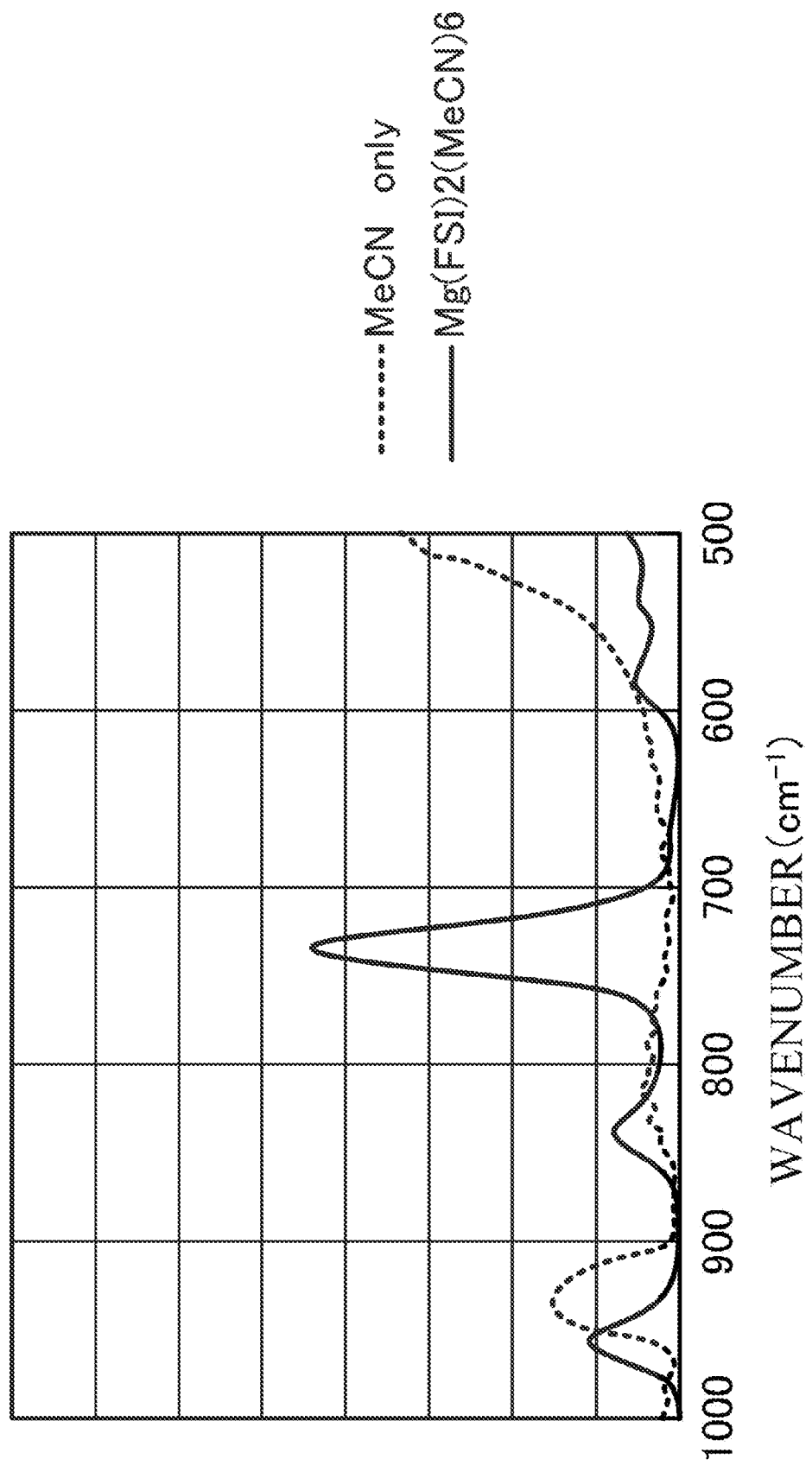
FIG. 3 is a chart obtained from Raman measurement for a white crystal obtained in Example 2 and acetonitrile.
Figure 4:
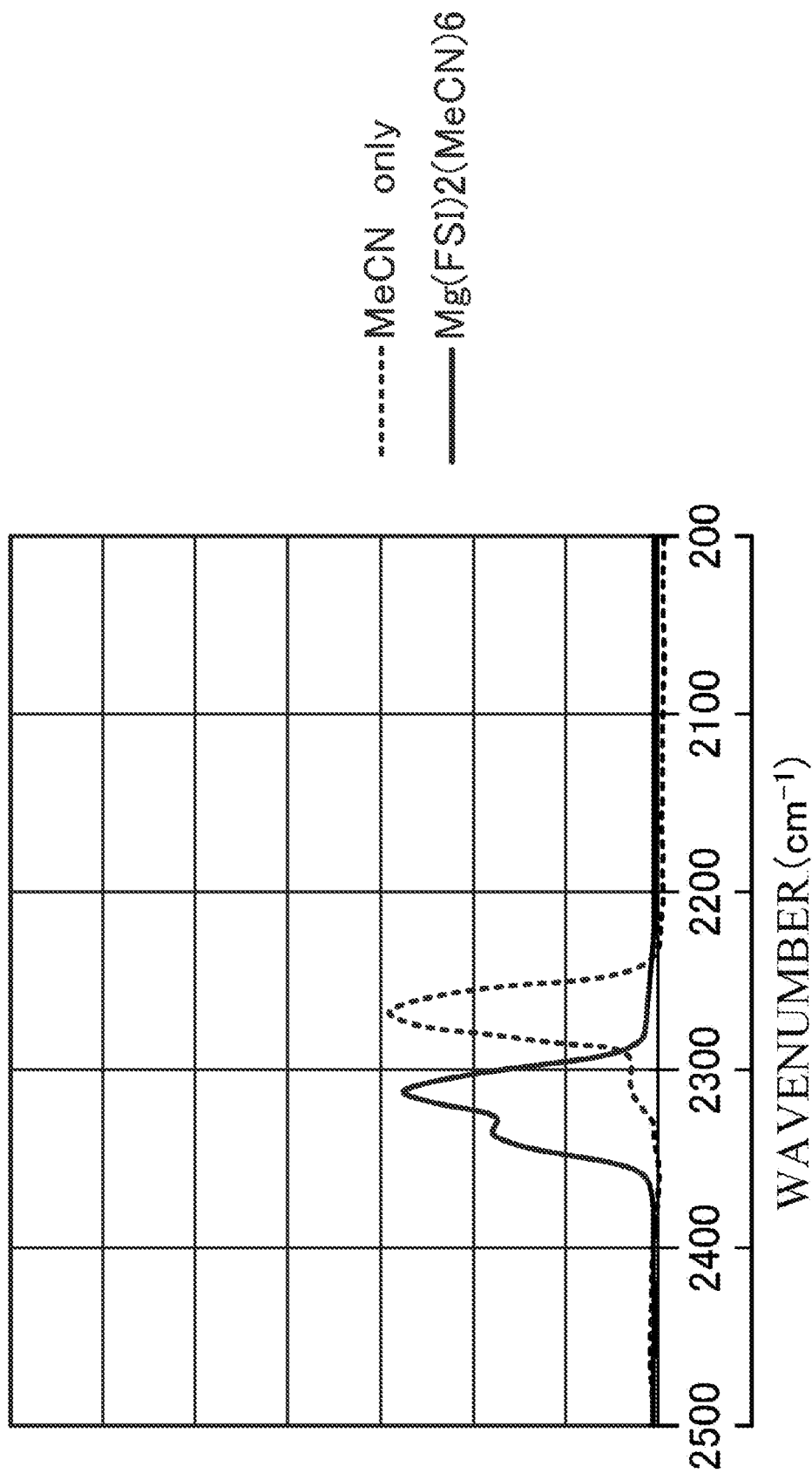
FIG. 4 is a chart obtained from Raman measurement for the white crystal obtained in Example 2 and acetonitrile.

As a result of comparison in Raman measurement between the resultant product (the white crystal) and acetonitrile, stretching vibration derived from FSI was observed at 731 $cm^{-1}$ in the product (FIG. 3). Moreover, it has been confirmed that stretching vibration due to acetonitrile shifts from 2264 $cm^{-1}$ to 2310 $cm^{-1}$ due to coordination to $Mg(FSI)_2$ (FIG. 4).

Example 3

Synthesis of $Mg(FSI)_2(MeCN)_5$

The product obtained in Example 1 was pressure-reduced for two hours at a room temperature in a pressure reduction oven (fully vacuumed). In this manner, white powder was obtained.

As a result of $^{19}F$-NMR measurement for the resultant product, only a single peak derived from $Mg(FSI)_2$ was confirmed at δ=55.9 ppm. As a result of $^1H$-NMR measurement, a single peak derived from acetonitrile was confirmed at δ=2.06 ppm. From an integrated value ratio with respect to an internal standard (using benzenesulfonyl fluoride) in these NMR results, it has been confirmed that the resultant product is $Mg(FSI)_2(MeCN)_5$. As a result of KF measurement, the amount of moisture in the product was 210 mass ppm.

Example 4

Synthesis of $Mg(FSI)_2(MeCN)_4$

The product obtained in Example 1 was pressure-reduced for three hours at 50° C. in a pressure reduction oven (fully vacuumed). In this manner, translucent viscous liquid was obtained.

As a result of $^{19}F$-NMR measurement for the resultant product, only a single peak derived from $Mg(FSI)_2$ was confirmed at δ=55.9 ppm. As a result of $^1H$-NMR measurement, a single peak derived from acetonitrile was confirmed at δ=2.05 ppm. From an integrated value ratio with respect to an internal standard (using benzenesulfonyl fluoride) in these NMR results, it has been confirmed that the resultant product is $Mg(FSI)_2(MeCN)_4$. As a result of KF measurement, the amount of moisture in the product was 270 mass ppm.

Example 5

Synthesis of $Mg(FSI)_2(DMC)_3$

A large excess (about 80 equivalent) of dimethyl carbonate (DMC, a moisture amount of 20.7 mass ppm) was added to the product obtained in Example 1, and a lower layer of two layers was recovered. Thereafter, the resultant was pressure-reduced for two hours at a room temperature in a pressure reduction oven (fully vacuumed). In this manner, a light-yellow product in the form of high-viscosity liquid was obtained.

As a result of $^{19}$F-NMR measurement for the resultant product, only a single peak derived from $Mg(FSI)_2$ was confirmed at δ=55.9 ppm. As a result of $^1$H-NMR measurement, a single peak derived from dimethyl carbonate was confirmed at δ=3.69 ppm. From an integrated value ratio with respect to an internal standard (using benzenesulfonyl fluoride) in these NMR results, it has been confirmed that the resultant product is $Mg(FSI)_2(DMC)_3$.

Example 6

Synthesis of $Mg(FSI)_2(G1)_3$

A large excess (about 100 equivalent) of 1,2-dimethoxyethane (G1, a moisture amount of 143 mass ppm) was added to the product obtained in Example 1, and the resultant mixture solution was condensed by an evaporator. Thereafter, the resultant was pressure-reduced for 30 minutes at 70° C. in a pressure reduction oven (fully vacuumed). In this manner, a light-yellow product in the form of high-viscosity liquid was obtained.

As a result of $^{19}$F-NMR measurement for the resultant product, only a single peak derived from $Mg(FSI)_2$ was confirmed at δ=55.9 ppm. As a result of $^1$H-NMR measurement, a single peak derived from 1,2-dimethoxyethane was confirmed at each of δ=3.42 ppm and δ=3.23 ppm. From an integrated value ratio with respect to an internal standard (using benzenesulfonyl fluoride) in these NMR results, it has been confirmed that the resultant product is $Mg(FSI)_2(G1)_3$.

Example 7

Synthesis of $Mg(FSI)_2(MeCN)_1(G3)_1$ 1 equivalent of triethylene glycol dimethyl ether (triglyme, G3, a moisture amount of 254 mass ppm) was added to the product obtained in Example 1, and the resultant mixture solution was condensed by an evaporator (55° C., 30 hPa). In this manner, a colorless product in the form of viscous liquid was obtained.

As a result of $^{19}$F-NMR measurement for the resultant product, only a single peak derived from $Mg(FSI)_2$ was confirmed at δ=50.8 ppm. As a result of $^1$H-NMR measurement, multiple split peaks were confirmed at δ=3.50 to 3.49 ppm and 3.42 to 3.40 ppm, a single peak was confirmed at 3.22 ppm, and the presence of triglyme was confirmed. Moreover, a single peak derived from acetonitrile was confirmed at δ=2.05 ppm. From an integrated value ratio with respect to an internal standard (using trifluorotoluene) in these NMR results, it has been confirmed that the resultant product is $Mg(FSI)_2(MeCN)_1(G3)_1$.

Example 8

Synthesis of $Mg(FSI)_2(G3)_2$ 2 equivalent of triethylene glycol dimethyl ether (triglyme, G3, a moisture amount of 254 mass ppm) was added to the product obtained in Example 1, and the resultant mixture solution was condensed by an evaporator (60° C., 10 hPa). In this manner, a white product in the form of viscous solid was obtained.

As a result of $^{19}$F-NMR measurement for the resultant product (in the form of white viscous solid), only a single peak derived from $Mg(FSI)_2$ was confirmed at δ=50.8 ppm. As a result of $^1$H-NMR measurement, multiple split peaks were confirmed at δ=3.50 to 3.48 ppm and 3.42 to 3.40 ppm, a single peak was confirmed at 3.22 ppm, and the presence of triglyme was confirmed. Moreover, a single peak derived from acetonitrile was confirmed at δ=2.05 ppm. From an integrated value ratio with respect to an internal standard (using trifluorotoluene) in these NMR results, it has been confirmed that the resultant product is $Mg(FSI)_2(G3)_2$. As a result of KF measurement, the amount of moisture in the product was 448 mass ppm.

Figure 5:
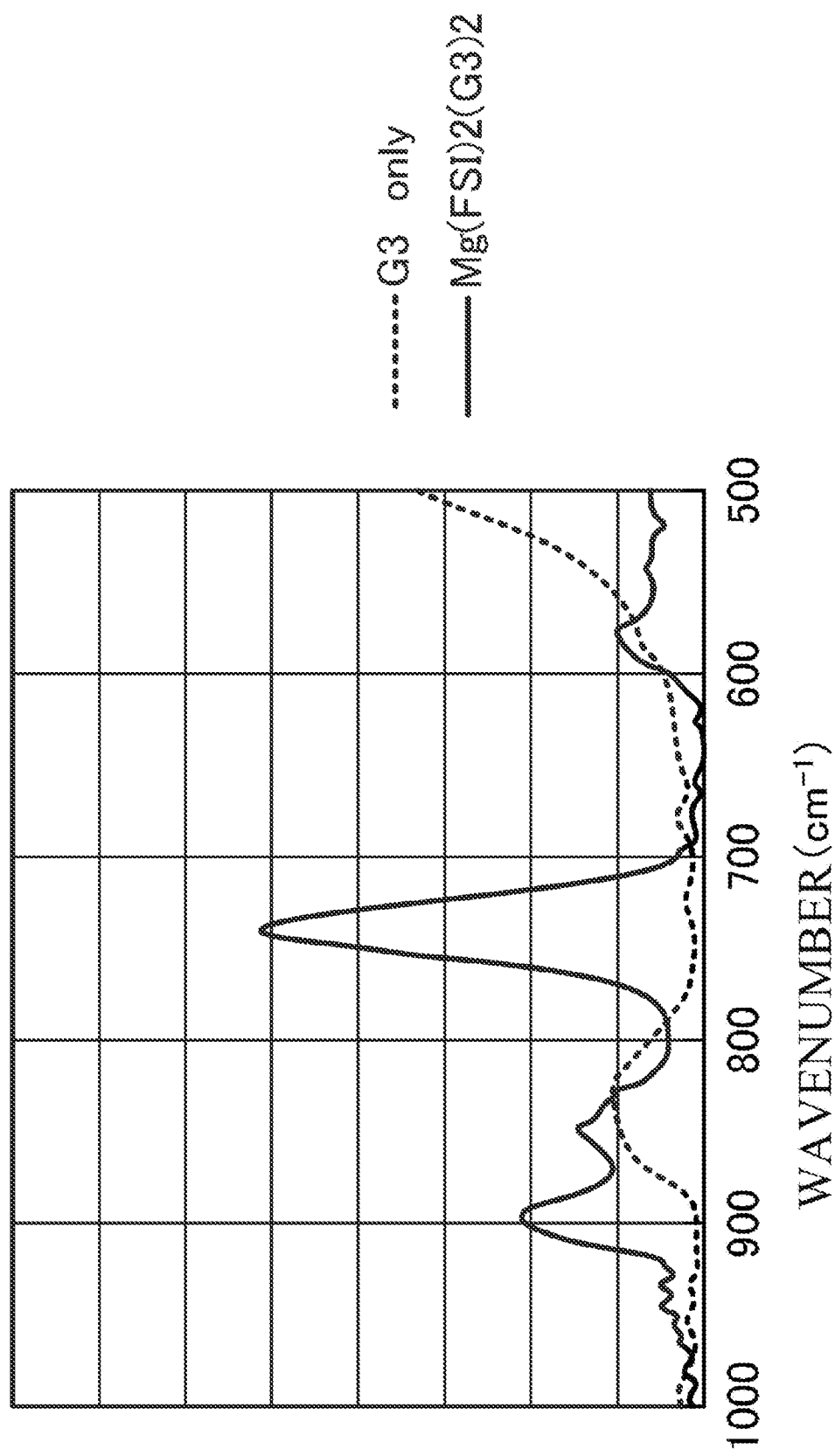
FIG. 5 is a chart obtained from Raman measurement for a product in the form of white viscous solid obtained in Example 8 and triglyme.

As a result of comparison in Raman measurement between the resultant product (in the form of white viscous solid) and triglyme, stretching vibration derived from FSI was observed at 731 cm$^{-1}$ in the product. Moreover, it has been confirmed that stretching vibration due to triglyme shifts from 840 cm$^{-1}$ to 892 cm$^{-1}$ due to coordination to $Mg(FSI)_2$ (FIG. 5).

Example 9

Synthesis of $Mg(FSI)_2(G3)_3$ 3 equivalent of triethylene glycol dimethyl ether (triglyme, G3, a moisture amount of 254 mass ppm) was added to the product obtained in Example 1, and the resultant mixture solution was condensed by an evaporator (60° C., 10 hPa). In this manner, a product in the form of clear colorless liquid was obtained.

As a result of $^{19}$F-NMR measurement for the resultant product (in the form of clear colorless liquid), only a single peak derived from $Mg(FSI)_2$ was confirmed at δ=50.8 ppm. As a result of $^1$H-NMR measurement, multiple split peaks were confirmed at δ=3.50 to 3.48 ppm and 3.42 to 3.40 ppm, a single peak was confirmed at 3.22 ppm, and the presence of triglyme was confirmed. From an integrated value ratio with respect to an internal standard (using trifluorotoluene) in these NMR results, it has been confirmed that the resultant product is $Mg(FSI)_2(G3)_3$. As a result of KF measurement, the amount of moisture in the product was 455 mass ppm.

Example 10

Synthesis of $Mg(FSI)_2(G3)_5$ 5 equivalent of triethylene glycol dimethyl ether (triglyme, G3, a moisture amount of 254 mass ppm) was added to the product obtained in Example 1, and the resultant mixture solution was condensed by an evaporator (60° C., 10 hPa). In this manner, a product in the form of clear colorless liquid was obtained.

As a result of $^{19}$F-NMR measurement for the resultant product (in the form of clear colorless liquid), only a single peak derived from $Mg(FSI)_2$ was confirmed at δ=50.8 ppm. As a result of $^1$H-NMR measurement, multiple split peaks were confirmed at δ=3.50 to 3.48 ppm and 3.42 to 3.40 ppm, a single peak was confirmed at 3.22 ppm, and the presence of triglyme was confirmed. From an integrated value ratio with respect to an internal standard (using trifluorotoluene) in these NMR results, it has been confirmed that the resultant product is Mg(FSI)$_2$(G3)$_5$. As a result of KF measurement, the amount of moisture in the product was 253 mass ppm.

INDUSTRIAL APPLICABILITY

According to the present invention, e.g., a new bis(fluorosulfonyl)imide compound can be provided. Such a compound can be used as an electrolyte or an additive, for an electrolytic solution for example. For example, a compound containing magnesium as the metal M can be used as a compound (e.g., an electrolyte) for a magnesium (ion) battery (a secondary battery).

The invention claimed is:

1. A compound comprising a structure represented by Formula (1) below:

$$M_aX_bY_c \qquad (1),$$

where M represents metal other than alkali metal, X represents —N(SO$_2$F)$_2$, Y represents a coordinating solvent, and a, b, and c are positive numbers; and
the coordinating solvent Y includes at least one type selected from a carbonate-based solvent, an ether-based solvent, an ester-based solvent, and a sulfone-based solvent.

2. The compound of claim 1, wherein
the metal M includes at least one metal type selected from group 2, 10 to 13 metals in a periodic table.

3. The compound of claim 1, wherein
the metal M includes group 2 metal in the periodic table.

4. The compound of claim 1, wherein
the coordinating solvent Y includes at least one type selected from linear carbonate, cyclic carbonate, linear aliphatic ether, cyclic ether, linear ester, cyclic ester, and cyclic sulfone.

5. The compound of claim 1, wherein
a water content is 5000 mass ppm or less.

6. The compound of claim 1, wherein
a ratio among a, b, and c is a/b/c=1/2 to 3/1 to 8.

7. The compound of claim 1, wherein
the metal M is magnesium,
the coordinating solvent Y includes at least one type selected from dimethyl carbonate, diethyl carbonate, ethyl methyl carbonate, ethylene carbonate, propylene carbonate, butylene carbonate, 1,2-dimethoxyethane, diethylene glycol dimethyl ether, triethylene glycol dimethyl ether, tetrahydrofuran, 2-methyltetrahydrofuran, 1,4-dioxane, 1,3-dioxolane, methyl acetate, ethyl acetate, ethyl propionate, propyl propionate, γ-butyrolactone, valerolactone, and sulfolane,
a water content is 5000 mass ppm or less, and
a ratio among a, b, and c is a/b/c=1/2 to 3/1 to 8.

8. A method for producing the compound of claim 1, comprising:
a reaction step of causing salt of the metal M causing no water in reaction and bis(fluorosulfonyl)imide to react with each other under a presence of a coordinating solvent.

9. The production method of claim 8, further comprising:
a ligand substitution step of obtaining, by means of a coordinating solvent Y1, a compound that the coordinating solvent Y is Y1 in Formula (1) at the reaction step and subsequently substituting at least part of the coordinating solvent Y1 with a coordinating solvent Y2.

10. The production method of claim 9, wherein
the coordinating solvent Y1 is a nitrile-based solvent, and the coordinating solvent Y2 is at least one type selected from a carbonate-based solvent, an ether-based solvent, an ester-based solvent, and a sulfone-based solvent.

11. The production method of claim 8, wherein
the salt of the metal M is at least one type selected from halide, sulfate, nitrate, phosphate, chlorate, chromate, formate, acetate, and trifluoromethanesulfonate.

12. The production method of claim 8, wherein 0.3 to 1.5 equivalent of the salt of the metal M is used for the bis(fluorosulfonyl)imide.

13. The production method of claim 8, wherein
at the reaction step, the reaction is made with a moisture amount of 5000 mass ppm or less in a reaction system.

14. The production method of claim 8, further comprising:
a step of recrystallizing the generated compound represented by Formula (1).

15. A compound comprising a structure represented by Formula (1) below:

$$M_aX_bY_c \qquad (1),$$

where M represents metal other than alkali metal, X represents —N(SO$_2$F)$_2$, Y represents a coordinating solvent, and a, b, and c are positive numbers;
a water content is 5000 mass ppm or less; and
the metal M includes at least one metal type selected from group 2 to 11, 13 to 15 metals in a periodic table,
wherein a ratio among a, b, and c is a/b/c=1/2 to 3/1 to 8.

16. The compound of claim 15, wherein
the metal M includes group 2 metal in the periodic table.

17. The compound of claim 15, wherein
the coordinating solvent Y includes at least one type selected from a nitrile-based solvent, a carbonate-based solvent, an ether-based solvent, an ester-based solvent, and a sulfone-based solvent.

18. The compound of claim 15, wherein
the coordinating solvent Y includes at least one type selected from aliphatic nitrile, linear carbonate, cyclic carbonate, linear aliphatic ether, cyclic ether, linear ester, cyclic ester, and cyclic sulfone.

19. The compound of claim 15, wherein
the metal M is magnesium,
the coordinating solvent Y includes at least one type selected from acetonitrile, dimethyl carbonate, diethyl carbonate, ethyl methyl carbonate, ethylene carbonate, propylene carbonate, butylene carbonate, 1,2-dimethoxyethane, diethylene glycol dimethyl ether, triethylene glycol dimethyl ether, tetrahydrofuran, 2-methyltetrahydrofuran, 1,4-dioxane, 1,3-dioxolane, methyl acetate, ethyl acetate, ethyl propionate, propyl propionate, γ-butyrolactone, valerolactone, and sulfolane.

* * * * *